United States Patent [19]

Amschler

[11] 4,108,982

[45] Aug. 22, 1978

[54] 4-(2-IMIDAZOLIN-2-YL) AMINOPYRAZOLES

[75] Inventor: Hermann Amschler, Radolfzell, Germany

[73] Assignee: Byk Gulden Lomberg Chemische Fabrik GmbH, Germany

[21] Appl. No.: 733,866

[22] Filed: Oct. 19, 1976

[30] Foreign Application Priority Data

Oct. 20, 1975 [LU] Luxembourg ............................ 73608

[51] Int. Cl.² ...................... C07D 403/12; A61K 7/15
[52] U.S. Cl. ...................................... 424/73; 548/316; 548/320; 548/358; 260/307 F; 424/70; 424/272; 424/273 P
[58] Field of Search ......................... 260/309.6, 309.7; 424/273

[56] References Cited

U.S. PATENT DOCUMENTS

| | | | |
|---|---|---|---|
| 3,954,757 | 5/1976 | Arya et al. | 260/309.6 |
| 3,979,408 | 9/1976 | Trani | 260/309.6 |

OTHER PUBLICATIONS

Pollak et al., Monatshefte fur Chemie 1972, vol. 103, pp. 1591–1603.
Verge et al., Chem. Abst. 1975, vol. 83, No. 10079k.

*Primary Examiner*—Natalie Trousof

*Attorney, Agent, or Firm*—Berman, Aisenberg & Platt

[57] ABSTRACT

Physiologically-active and pharmaceutically-acceptable 4-aminopyrazoles of each of the formulae

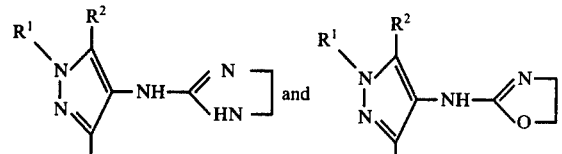

(Ia)           (Ib)

wherein each of
$R^1$, $R^2$ and $R^3$ is, independently, e.g., a hydrogen atom (—H), aliphatic hydrocarbyl, alicyclic hydrocarbyl, phenyl, substituted phenyl, phenalkyl or nuclearly-substituted phenalkyl.

and their pharmacologically-acceptable acid-addition salts are synthesized by known procedures from available starting materials or from compounds which are made by analogy procedures from known compounds. The subject 4-aminopyrazoles and their pharmacologically-acceptable acid-addition salts are prepared in the form of medicament compositions and used as diuretics, saluretics and/or antihypertensives.

11 Claims, No Drawings

4-(2-IMIDAZOLIN-2-YL) AMINOPYRAZOLES

BACKGROUND 4-aminopyrazoles of formula III and processes for their production are known, for example, from the article by S. F. Torf, N. I, Kudryashova, N. V. Khromov-Borisov and T. A. Mikhailova, Zh. Obshsh. Khim., 32, 1740-6, 1962, abstracted in Chem. Abstr., 58, 4540, 1963. Those 4-aminopyrazoles of formula III (required as starting material for producing compounds of formula I), which have not yet been described in the literature, are produced from known compounds by this process. Analogously, other desired compounds III are obtained.

1-aroylimidazolidin-2-ones are obtained by reacting the corresponding aroyl halides, preferably chlorides, with ethylene urea.

Chem. Abstr., 58, 4540, 1963, fails to present a statement regarding pharmacological action. In Chem. Abstr., 68, P 78 283 t, 1968, analgesic and antipyretic action is attributed to 1-phenyl-4-aminopyrazoles.

The present specification discloses and exemplifies two distinct inventions based on structurally-related, but independent and distinct, active principles. Only one of these inventions is herein claimed. The other invention is claimed in Dr. Walter Krastinat's concurrently-filed application.

Throughout the entire text all references to specific oxazolinaminopyrazoles are equally applicable to their imidazolinaminopyrazole counterparts; examples of either are regarded as illustrative of their respective counterparts.

SUMMARY OF THE INVENTIONS

These inventions have three distinct aspects: (a) therapeutically-acceptable substituted —— 4-[2-(oxazolin- or -imidazolin)-2-yl] aminopyrazoles and their pharmacologically-acceptable acid-addition salts, (b) medicament compositions in which one or a combination of compounds under (a) is an active component or principle and (c) the use of one or a combination of compounds under (a) as diuretics, saluretics and/or antihypertensives. The aminopyrazoles are of one of the formulae (Ia) and (Ib)

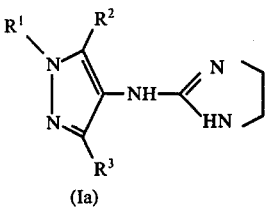

(Ia)

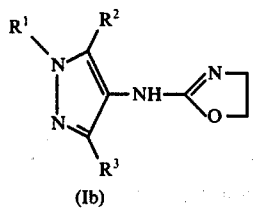

(Ib)

wherein each of $R^1$, $R^2$ and $R^3$ is, independently, e.g., a hydrogen atom (-H), aliphatic hydrocarbyl, alicyclic hydrocarbyl, phenyl, substituted phenyl, phenalkyl or nuclearly-substituted phenalkyl.

Throughout the disclosure meanings for $R^1$, $R^2$ and $R^3$ apply equally to compounds of formula Ia, those of formula Ib and their respective acid-addition salts. Suitable ring substituents for the substituted phenyl and for the substituted phenylalkyl includes, e.g., halo (e.g. fluoro, bromo and, preferably, chloro), alkyl having from 1 to 4 carbon atoms (e.g. methyl, ethyl, propyl, isopropyl and butyl), alkoxy having from 1 to 4 carbon atoms (e.g. methoxy, ethoxy, propoxy, isopropoxy and butoxy), alkylmercapto (e.g. methylmercapto, ethylmercapto, propylmercapto, isopropylmercapto and butylmercapto), trifluoromethyl and nitro, but such substituents are not so limited. The sole limitations of the substituents or, for that matter, of the meanings of $R^1$, $R^2$ and $R^3$ is that they do not render the aminopyrazole unduly toxic and they do not negate the diuretic, the saluretic and the antihypertensive activity of the aminopyrazole.

DETAILS

The inventions relate to 4-aminopyrazoles of formula I:

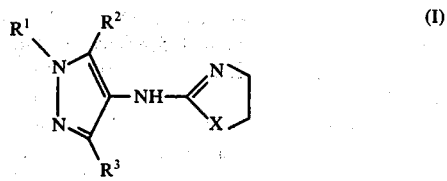

(I)

wherein each of $R^1$, $R^2$ and $R^3$ has its previously-ascribed meaning, and

X is an oxygen atom or an NH group, and their pharmacologically-tolerated acid-addition salts.

Hydrocarbyl is a monovalent radical composed entirely of carbon and hydrogen atoms appropriately bonded together.

Aliphatic hydrocarbyl includes, e.g., straight-chained and branched-chained alkyl with from 1 to 7 carbon atoms, preferably lower alkyl with from 1 to 4 carbon atoms, and especially with 1 or 2 carbon atoms, e.g. methyl, ethyl, propyl, butyl, pentyl, hexyl, heptyl, isopropyl, sec-butyl, tert-butyl, neopentyl, 3-methylbutyl, 2-methylpentyl, 3,3-dimethylbutyl and 2-ethyl-3-methylbutyl.——Alicyclic hydrocarbyl includes, e.g., cycloalkyl radicals with from 3 to 7 ring carbon atoms, for example cyclopropyl, cyclobutyl, cyclopentyl, cyclohexyl and cycloheptyl, of which those with 5 or 6 carbon atoms are preferred. Alicyclic rings are optionally lower-alkyl substituted.

Phenylalkyl (or phenalkyl) includes groups in which the alkyl part has from 1 to 4 carbon atoms and in which the phenyl is located at any point in the alkyl chain, preferably in the α-position, e.g., benzyl, α- or β-phenylethyl, α- or γ-phenylpropyl and α- or δ-phenylbutyl, of which α-phenylethyl and, especially, benzyl are preferred.

The phenyl group, is optionally substituted in any position, preferably with 1 or 2 substituents which are the same or different; the energetically-favored positions are preferred. Suitable substituents include halogen atoms, for example fluoro, bromo and, preferably, chloro; alkyl, alkoxy or alkylmercapto (each with from 1 to 4 carbon atoms); trifluoromethyl and nitro. Examples of substituted phenyl or o-chlorophenyl, m-chlorophenyl, p-chlorophenyl, m-bromophenyl, p-bromophenyl, p-fluorophenyl, m-tolyl, p-tolyl, 3,4- dichlorophenyl, 3-chloro-p-tolyl, α,α,α-trifluoro-m-tolyl p-nitrophenyl, m-nitrophenyl, p-methoxyphenyl, p-ethoxyphenyl, 3,4-dimethoxyphenyl, cumenyl, p-butylmercaptophenyl and 3,4-dimethylphenyl, of which p-substituted phenyl, mainly p-halophenyl (especially p-chlorophenyl), p-methoxyphenyl and p-tolyl are preferred. The phenylalkyl group is also similarly optionally substituted, inter alia, by halogen atoms, e.g. fluoro, chloro or bromo and by alkyl and alkoxy with from 1 to 4 carbon atoms. Illustrative examples are: p-chlorobenzyl, m-chlorobenzyl, p-bromobenzyl, o-fluorobenzyl, p-fluorobenzyl, p-methoxybenzyl, p-methylbenzyl, α-(p-bromophenyl)ethyl, α-(p-tolyl)ethyl, α-(p-chlorophenyl)ethyl, (3-chloro-4-methylphenyl)ethyl, α-(3,4-dichlorophenyl)ethyl, p-isopropylbenzyl and 4-methyl-3-trifluoromethylbenzyl, of which those with a single substituent are preferred.

Pharmacologically-compatible salts encompass all those of inorganic and organic acids usually employed in pharmaceutical chemistry. Examples are pharmacologically-acceptable acid-addition salts which are either water-soluble or water-insoluble salts, such as the hydrochloride, hydrobromide, phosphate, nitrate, sulfate, acetate, citrate, gluconate, benzoate, hibenzate [2-(4-hydroxybenzoyl)benzoate], fendizoate {o-[(2'-hydroxy-4-biphenylyl)carbonyl]benzoate}, propionate, butyrate, sulfosalicylate, maleate, laurate, malate, fumarate, succinate, oxalate, tartrate, amsonate (4,4'-diaminostilbene-2,2'-disulfonate), embonate (1,1'-methylene-bis-2-hydroxy-3-naphthoate), metembonate, stearate, tosylate (p-toluenesulfonate), 2-hydroxy-3-naphthoate, 3-hydroxy-2-naphthoate and mesilate (methanesulfonate), as well as salts of bumetanid [3-(butylamino-)-4-phenoxy-5-sulfamoylbenzoic acid], furosemid (4-chloro-N-furfuryl-5-sulfamoylanthranilic acid), besunid [4-benzyl-3-butylamino-5-sulfamoylbenzoic acid], piretanid [4-phenoxy-3-(1-pyrrolidinyl)-5-sulfamoylbenzoic acid], etacrynic acid {[2,3-dichloro-4-(2-methylenebutyryl)phenoxy]acetic acid} and tienilic acid {[2,3-dichloro-4-(2-thenoyl)phenoxy]acetic acid}.

A select group of compounds of the invention includes substituted 4-aminopyrazoles of formula I*:

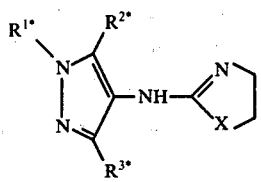

(I*)

wherein
R¹* is a hydrogen atom (-H), lower alkyl, cycloalkyl, phenyl, mono-substituted phenyl (the substituent being halo, lower alkyl or lower alkoxy), disubstituted phenyl (the substitutents being alike or different and signifying halo, lower alky or lower alkoxy, phenylalkyl, monosubstituted phenylalkyl (the substituent being halo, lower alkyl or lower alkoxy), disubstituted phenylalkyl (the substituents being alike or different an signifying halo, lower alkyl or lower alkoxy);

each of R²* and R³* is, independently, lower alkyl, phenyl, monosubstituted phenyl (the substituent being halo, lower alkyl or lower alkoxy), disubstituted phenyl (the substituents being alike or different and signifying halo, lower alkyl or alkoxy); and X is an oxygen atom (—O—) or an NH group; and their pharmacologically-tolerable acid-addition salts.

A more special group of substituted 4-aminopyrazoles is composed of those of formula I**:

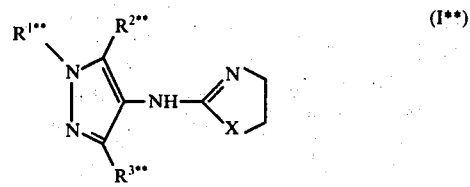

(I**)

wherein
R¹** is a hydrogen atom (—H), lower alkyl, cyclohexyl, phenyl, p-chlorophenyl, p-tolyl or benzyl;
R²** is lower alkyl or phenyl;
R³** is lower alkyl; and
X is an oxygen atom or an NH group;
and their pharmacologically-tolerable acid-addition salts.

Preferred 4-aminopyrazoles are those of formula I** wherein
R¹** is a hydrogen atom (—H), methyl, ethyl or phenyl;
R²** is methyl, ethyl or phenyl;
R³** is methyl or ethyl; and
X is an oxygen atom or, especially, an NH group, and their pharmacologically-tolerable acid-addition salts.

Illustrative compounds are 3,5-dimethyl-4-(2-imidazolin-2-yl)aminopyrazole, 1,3,5-trimethyl-4-(2-imidazolin-2-yl)aminopyrazole, 1-methyl-3,5-diethyl-4-(2-imidazolin-2-yl)aminopyrazole, 3-methyl-1,5-diphenyl-4-(2-imidazolin-2-yl)aminopyrazole, 1,3,5-trimethyl-4-(2-oxazolin-2-yl)aminopyrazole, 1,3-dimethyl-5-phenyl-4-(2oxazolin-2-yl)aminopyrazole and their pharmacologically-tolerable acid-addition salts.

The inventions also relate to a process for producing compounds of formula I and their pharmacologically-tolerable acid-addition salts. The process is characterized by using known methods to cyclize a 4-aminopyrazole of formula II:

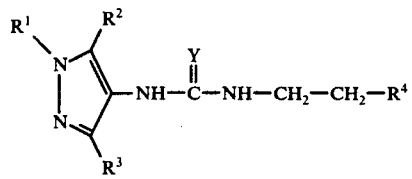

(II)

wherein
R¹, R² and R³ have their previously-ascribed meanings;
R⁴ is halo (preferably bromo or, especially, chloro) or—NH₂; and
Y is =O, =S or =NH;
or an acid-addition salt thereof, and (if desired) subsequently converting any salts obtained into the corresponding free base or into other salts. Alternatively, the obtained base is converted into an acid-addition salt.

The cyclization is carried out according to known methods. Thus, it is effected, e.g., thermally without solvent or by heating a solution or suspension (alone or with the addition of acceptors, for example metallic oxides or salts, for the components which are split off during cyclization).

For producing compounds of formula I in which X = NH, it is advantageous in the thermal cyclization of compounds of formula II (in which Y = NH, $R^4$ = $NH_2$) to start with such compounds of formula II in acid-addition salt (prepared in situ) form. The reaction is conducted by heating the reaction mixture, for example, to a temperature in the range of from 140° to 170° C for from 0.5 to 5 hours.

Cyclization of compounds of formula II (in which Y = S, $R^4$ = $NH_2$) is effected by heating a solution or suspension in a suitable solvent, such as ethanol, in the presence of (i.e. in contact with) metalic oxide, for example mercuric oxide or cupric oxide, or of a metal salt, for example mercuric or cupric acetate.

For producing compounds of formula I in which X = O, it is advantageous to carry out the cyclization thermally, starting with compounds of formula II in which $R^4$ is halo, for example chloro, and Y is =O. In a preferred form the cyclization is effected by suspending the starting compounds in a suitable solvent, for example water, then pouring the resulting admixture into a prepared volume of boiling water and heating it further only for a short period of time. In this way the formation of undesirable by-products is substantially avoided.

The obtained salt, for example the hydrochloride, is converted by neutralization with aqueous sodium or potassium hydroxide into the corresponding free base, which is then recovered by solvent extraction with a suitable solvent, such as ethyl acetate, which is not miscible with water. The free base is als obtained by neutralizing an acid-addition salt with sodium methylate in methanol and isolating the base by known processes. The salts are also covered into corresonding free bases by ion exchange. For this purpose a basic anion exchange resin, for example Amberlite IRA 400, is used.

An acid-addition salt is obtained by dissolving a free base in a suitable solvent, for example acetone, water or a low-molecular weight aliphatic alcohol (ethanol, isopropanol), which contains the desired acid or to which the desired acid is subsequently added. The salt is recovered by filtration, by precipitation with a non-solvent for the addition salt or by evaporation of the solvent.

The initial or starting compounds of formula II are produced by processes known to the technician from the corresponding 4-aminopyrazoles of formula III

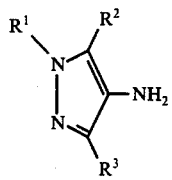

(III), in which $R^1$, $R^2$, $R^3$ have their previously-ascribed meanings. Thus, reaction with ammonium thiocyanate leads to the 4-thioureidopyraolzes, which are also obtained by reacting 4-aminopyrazoles (III) with benzoyl isothiocyanate, followed by hydrolysis. Alkylation of 4-thioureidopyrazoles with, e.g., methyl iodide, methyl bromide or diethyl sulfate, yields corresponding S-alkylpyrazolyl-isothiuronium salts, the reaction of which with ethylenediamine leads to 4-aminopyrazoles (II) [in which Y = NH and $R^4$ = $NH_4$] which are generally employed in situ for producing compounds according to the invention. Compounds of formula II are, alternatively, prepared from 4-aminopyrazoles of formula III, which are reacted with $CSCl_2$ to form 4-isothiocyanatopyrazoles, which are then converted (with ethylenediamine) into compounds of formula II in which $R^4$ = $NH_2$ and Y = S. Initial compounds of formula II in which Y = O are obtained, for example, by the addition of β-chloroethylisocyanate on to 4-aminopyrazoles of formula III.

Compounds of formula I, in which X repr4sents an NH group, are also obtained by reacting 4-aminopyrazoles of formula III with 1-aroylimidazolidin-2-ones in the presence of (i.e., in contact with) phosphorus oxychloride, followed by meutralization and hydrolysis. Intermediate products obtained after neutralization of the acid reaction mixture are aroyl derivatives which carry the aroyl radical on a nitrogen of the imidazoline. From these aroyl derivatives, which are obtained in pure form, the aroyl radical is very easily separated by saponification, thus yielding the compounds of the invention in particularly pure form.

An object of one invention is therefore also a process for producing substituted 4-aminopyrazoles of formula Ia and their pharmacologically-tolerated acid-addition salts, wherein a 4-aminopyrazole of formula III is reacted with a 1-aroylimidazolidin-2-one of formula IV:

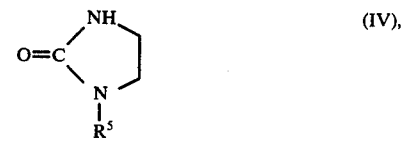

(IV), in which $R^5$ represents, e.g., a benzoyl radical which is optionally substituted by alkyl containing 1 or 2 carbon atoms, in the presence of at least 2 moles of phosphorus oxychloride per mole of 4-aminopyrazole, the resulting intermediate product is hydrolyzed after separation of excess phosphorus oxychloride, and the aroyl radical, $R^5$, is split off from the intermediate product by treatment with alcohol, acid, or a compound having an alkaline reaction. A thus-obtained salt is optionally converted into the corresponding free base or into other salts, or a free base is converted into an acid-addition salt, these procedures being entirely conventional and well known to the artisan.

As a rule the reaction is carried out at temperatures varying from room temperature (about 20° C) to a maximum of the boiling temperature of phosphorus oxychloride. 4-aminopyrazoles (III) and the 1-aroylimidazolidin-2-one (IV) are generally used in aproximately equimolar amounts. This is not critical, however, and either of the reaction partners is optionally used in a slight excess, for example an excess of from about 10 to about 20%, based on the amount of the other reaction partner. Even with a considerably larger excess of either the reaction proceeds in the same direction, but certain losses of yield are to be expected.

At least 3 moles of phosphorus oxychloride are expediently used per mole of 4-aminopyrazole (III). The simultaneous use of phosphorus oxychloride as solvent for the reaction partners is particularly preferred. Alternatively, an inert organic solvent, for example a chlorinated hydrocarbon, is employed as reaction medium.

On completion of the reaction excess phosphorus oxychloride is removed, preferably by distillation. The acid evaporation residue then contains a phosphorus-containing intermediary product, which ordinarily crystallizes and, when treated with water, or, still more quickly, with aqueous alkaline media, for example a sodium carbonate solution is hydrolyzed in the cold state. This hydrolysis is effected, e.g., both by direct addition of the aqueous medium to the evaporation residue or by dissolving the latter in an organic solvent, for example methylene chloride, and treating the resulting solution with ice-cooled water or an aqueous alkaline solution.

The optionally-substituted aroyl group is split off either with mineral acid or organic acid, such as acetic acid, or else with a reactant having an alkaline reaction, such as a sodium hydroxide solution, a potassium hydroxide solution, soda, ammonia, primary, secondary, or tertiary amine, such as an alkyl amine, for example n-butyl amine, ethanolamine, benzylamine or piperidine, or an alkali-metal alcoholate. The medium used for the separation does not ordinarily require a solvent; separation is effected, e.g., with a dilute acid or alkali solution or with an organic amine. In cases in which solubility is too limited, a suitable solvent or diluent is preferably added. Saponificaton is generally effected under heat, for example at a temperature between 60° and 120° C, expediently at the boiling temperature of the reaction medium, in order to avoid excessively long reaction times. The heating time is then generally more than 1hour, expediently several hours.

The aroyl radical is favorably split off with low (having up to 4 carbon atoms) aliphatic alcohols, preferably with primary alcohols. As a rule it is advisable to dissolve the aroyl compound in the alcohol and to boil it under reflux. When this procedure is adopted, the separation is very gentle and the yield, satisfactory.

Hydrolysis of the phosphorus-containing intermediate product and saponification of the formed aroyl derivatives of compounds of formula Ia are, alternatively, effected in one operation. To accomplish this, excess phosphorus oxychloride is removed from the reaction product of the condensation by distillation, whereupon the separating reactant, for example alcohol, is added directy and heated. The final product obtained after hydrolysis and saponification is nevertheless obtained in the completely-pure state, and the overall yield is satisfactory.

A reaction product of formula Ia is isolated either directly as a base or, after acidification, in acid-addition salt form. When the aroyl group is split off with acid, the salt, for example the hydrochloride, precipitates (in many cases) from the aqueous solution as a crystalline product and is obtained in the pure state by filtration. Obtained salts are, when desired, converted into other salts, for example pharmacologically-tolerated salts, by way of the free base or by resalification.

ACTIVITY AND UTILITY

Surprisingly, compounds of formula I have a strong diuretic and saluretic activity combined with a simultaneous antihypertensive and, partly, heart-frequency reducing activity. They also exert an anti-migraine effect and, in addition, a pilomotoric activity.

Compounds with such an activity profile could not have been expected from prior art teachings. The 4-aminopyrazoles of formula I thus constitute a special class of substances as regards their particular pharmacological action, which must be regarded as an enrichment of the pharmaceutical armory and of cosmetics.

The excellent and differentiated activity of compounds of formula I and their salts makes them useful in human medicine. They are also useful in cosmetics.

Indications for human medicine include cardiac, renal, hepatogenous oedemata, oedema and toxicosis of pregnancy, adiposity with liquid retention, essential and secondary hypertension of all degrees of severity, as well as migraine, for all of which compounds of formula I and their acid-addition salts are useful.

In cosmetics these compounds are useful for erecting and strengthening hair, for example, in hair and shaving lotions as a pilomotoric product.

Compounds of formula I display a spectrum of pharmcological activity with different point of emphasis according to the specific substitution, one of the noted effects (particularly the diuretic and saluretic effect, the antihypertensive effect or a combination of these effects) being emphasized. As the specific therapeutic profile varies to some degree from compound to compound, the compound best suited for any particular application is selected on the basis of its own spectrum. The relevant therapeutic profile for each compound of formula I is readily determined by established routine procedures.

The surprising activity of these compounds distinctly surpasses (using standard methods) that of known active substances, for example spironolactone (diuretic), hydrochlorothiazide (diuretic, antihypertensive) and dihydralazine (antihypertensive).

The compounds with, for example, a primarily diuretic and saluretic action bring about a marked increase in excretion of water and electrolyte in the first few hours after administration to rats. $Na^+$ excretion particularly increases, while $K^+$ concentration falls markedly; the Na/K quotient is thus displaced in favor of potassium. The compounds with primarily an antihypertensive action continuously lower the systolic blood pressure of renal-hypertensive rats, but only exert a slight action on cardiac frequency. The compounds with a primary anti-migraine action reduce any tendency to migraine attack and cause a distinct improvement in general feeling.

In addition to the treatment of human disorders and/or of human hair, a further object of the inventions is to provide means for such treatment. These means are medicaments characterized by one or more active principles of formula I and/or of their pharmcologically-tolerable salts.

Diuretic, saluretic, antihypertensive or pilomotoric preparations according to the invention and those having a heart-frequency-reducing or anti-migraine action are produced according to known and well-established processes. As pharmaceutical products, the new compounds are used as such or, optionally, in combination with suitable pharmaceutical supports. When a pharmaceutical preparation contains a pharmaceutical support in addition to one or more active principles, the active-principle content of these mixtures is from 0.1 to 99.5, preferably from 0.5 to 95, percent by weight of the total mixture.

In the human medicine sphere the active principles of these inventions are used in any suitable form which produces or maintains an adequate blood level. Such forms include those regularly employed for oral or parenteral adminstration in suitable doses. Pharmaceutical preparations advantageously contain the active principle in the form of unit doses which are designed according to the nature of desired administration. A unit dose is, for example, a tablet, a pill, a capsule or a measured volume of a powder, a granulate, a solution, an emulsion or a suspension.

"Unit dose" (as used throughout this disclosure) is a physically-determined unit which contains an individual quantity of active cmponent in combination with a pharmaceutical support. The active-principle content therein corresponds to a fraction or a multiple of an individual therapeuctic dose. An individual dose preferably contains the quantity of active principle which is administered in a single application and which usually corresponds to a whole, a half, a third or a quarter of the daily dose. If, for an individual therapeutic administration, one only requires a fraction, such as the half or a quarter, of the unit dose, the unit dose is advantageously divisble, for example, in the form of a tablet with a notch.

Pharmaceutical preparations according to the inventions, when they are in unit doses and are intended for application, for example, to human beings, contain from about 0.1 to 500, advantageously from 0.5 to 100 and especially from 1 to 50, mg of active principle of formula I or acid-addition salt thereof.

It is generally advantageous in human medicine to administer active principle or principles of formula I (or acid-addition salt thereof) per os in a daily dose of from about 0.001 to about 5, preferably from 0.01 to 2 and especially from 0.05 to 1, mg/kg of body weight, optionally in the form of several, preferably 1 to 3, individual doses in order to achieve the desired results. An individual dose contains active principle or principles in quantities of from about 0.001 to about 2.5, preferably from 0.01 to 1.5 and especially from 0.05 to 0.5, mg/kg of body weight. For parenteral, for example intravenous, treatment similar dosages are used.

Therapeutic administration of a pharmaceutical preparation according to the inventions is carried out from one to four times a day at determined or variable points of time, for example after meals and/or in the evening. Actual doses do, at times, differ according to the nature, the body weight and the age of the patient being treated, the nature and severity of the disorder, the nature of the preparation and the application of the pharmaceutical product, as well as the interval within which administration occurs. In a few cases it is thus sufficeint to manage with less than the previously-noted quantity of active principle, whereas other cases require, e.g., an excess of the quantity of active principle mentioned. The optimum dosage and form of application of active principle required for each case is easily determined by any technician on the basis of his technical knowledge.

Pharmaceutical preparations generally consist of active principle according to the inventions and non-toxic therapeutically-compatible pharmaceutical support, which is in admixture with or a diluent for the active principle. The support is in a solid, semi-solid or liquid state or is an encapsulating agent, for example in the form of a capsule, a tablet coating, a bag or another container for the therapeutically-active component. A support serves, for example, as a vehicle for taking up the pharmaceutical by the body, as a formulation aid, as a sweetener, as a flavor corrector, as a coloring material or as a preservative. Supports are used singly or in any convenient combination.

For oral application suitable dosage forms are, e.g., tablets, pills, hard and soft capsules (for example of gelatin), dispersible powders, granulates, aqueous and oily suspensions, emulsions, solutions or syrups.

Tablets contain, e.g., inert diluents, such as calcium carbonate, calcium phosphate, sodium phosphate or lactose; granulating and distributing agents, such as maize starch or alginates; binders, such as starch, gelatin or acacia gum; and lubricants, such as aluminum or magnesium stearate, talcum or silicone oil. They are optionally additionally provided with a coating, which is, e.g., designed to bring about delayed solution and resorption of the pharmaceutical product in the gastrointestinal tract and consequently, for example, an improved compatibility, protraction or delayed action. Gelatin capsules contain, e.g., the pharmaceutical product mixed with a solid diluent, for example calcium carbonate or kaolin, or an oily diluent, for example olive oil, groundnut oil or liquid paraffin.

Aqueous suspensions contain, e.g., suspending agents, such as sodium carboxymethylcellulose, methylcellulose, hydroxypropylcellulose, sodium alginate, polyvinylpyrrolidone, gum dragon or acacia gum; dispersants and wetting agents, such as polyoxyethylene stearate, heptadecaethyleneoxycetanol, polyoxyethylene sorbitol mono-oleate, polyoxyethylene sorbitan mono-oleate or lecithin; preservatives, such as methyl or propyl hydroxybenzoates; flavoring and/or sweetener, such as saccharose, lactose, sodium cyclamate, dextrose or invert sugar syrup.

Oily suspensions contain, for example, groundnut oil, olive oil, sesame oil, coconut oil or liquid praffin and thickeners, such as beeswax, paraffin wax or cetyl alcohol, as well as sweetener, flavoring and/or antioxidant.

Powders and granulates dispersible in water contain the pharmaceutical product mixed, e.g., with dispersant, wetting agent and suspension agent, such as those previously mentioned, as well as with sweetener, flavoring and/or coloring material.

Emulsions contain, for example, olive oil, groundnut oil or liquid paraffin as well as emulsifier, such as acacia gum, gum dragon, phosphatides, sorbitan monooleate and polyoxyethylene sorbitan mono-oleate, as well as sweetener and flavoring material.

For parenteral administration of the pharmaceutical products aqueous suspensions for sterile injection, isotonic salt solutions or other solutions which optionally contain dispersant, wetting agent and/or pharmacologicaly-compatible diluent, for example propyleneglycol or butyleneglycol, are used.

In addition to compounds of the invention, the pharmaceutical preparations optionally contain one or more physiologically-compatible pharmacologically-active components belonging to other groups of pharmaceutical products. This is particularly indicated when the compounds of the inventions are used as anti-hypertensives, whereas medicaments having only one active principle are preferred for use as a diuretic/saluretic or as a means for treating migraine. Further active components (which are optionally incorporated in medicaments in combination with one or more active principles according to the inventions) are, e.g., triamterene, spironolactone, dihydralazine, mefruside, clopamide, chlorthalidone, furosemide, methyldopa, polythiazide, hydrochlorothiazide, reserpine, dihydroergocristine, rescinnamine and Rauwolfia total alkaloids.

Lotions, powders, ointments, pastes, cream, gels, sols or sprays suitable for cosmetic treatment contain, in addition to the active principle or principles according to the present invention, the usual supports, such as water, alcohol (for example ethanol and isopropanol), soap, animal or vegetable fat, wax, paraffin wax, starch, gum dragon, cellulose derivatives, polyethyleneglycols, silicones, bentonites, silica, talcum and zinc oxide or mixtures of these substances, whereas sprays additionally contain the usual propellants, such as chlorinated and fluorinated hydrocarbons. Cosmetic compositions of the inventions are advantageously in the form of solutions. Physiologically-compatible acids, such as adipic acid, citric acid or tartaric acid, as well as salts (which are acidic during hydrolysis), such as zinc chloride or aluminum chloride, exert an astringent action on the skin and are favorably incorporated in aqueous or aqueous-alcoholic solutions containing an active principle of these inventions. The usual solubilizers (for example, N,N-diethyl lactamide), skin care products, means for increasing skin smoothness (such as propyleneglycol and isopropyl myristate), astringents, menthol or antiseptics (for example boric acid, camphor, 8-hydroxyquinoline sulfate or p-hydroxybenzoic acid), as well as perfumes, are optionally included among ingredients of cosmetic compositions having, as an active principle, a compound of formula I or an acid-addition salt thereof.

The following Examples (in which mp means melting point and all temperatures are in ° C) explain the inventions in greater detail without restricting them. All references to following analogous procedures contemplate corresponding molar quantities of respective reactants.

EXAMPLE 1

($R^1$=H; $R^2$=$R^3$=$CH_3$; X=NH)

19.0 grams (g) of 3,5-dimethyl-4-aminopyrazole hydrochloride and 19.7 g of ammonium thiocyanate are dissolved in 100 milliliters (ml) of water, and the resulting solution is heated at boiling under reflux for 6 hours. Then the solution is concentrated to about 50 ml and cooled. Thus-formed precipitate is separated by filtration, washed with a little water and dried to yield 17.0 g of 3,5-dimethyl-4-thioureidopyrazole, mp 209° to 211°.

16.0 g of the noted thioureido compound and 27.0 g of methyl iodide are dissolved in 100 ml of methanol and heated to boiling under reflux for 2 hours. The resulting solution is concentrated in vacuo; the residue is mixed with 6.6 g of ethylenediamine; and the thus-obtained reaction mixture is cyclized by heating it for 2 hours in an oil bath at 160°. Residues of the gaseous reaction products are then driven off in vacuo. The viscous residue is dissolved in water; the resulting aqueous solution is extracted several times with diethylether and then concentrated by evaporation until crystallization takes place. The crystals which separate out are filtered off and dissoled again in water. The aqueous solution is mixed in portions with freshly-precipitated silver chloride and stirred intensively for 3 hours at room temperature. After filtering off the silver halide, the water is evaporated until crystallization takes place, thus yielding, 8.5 g of 3,5-dimethyl-4-(2-imidazolin-2-yl)aminopyrazole as the monohydrochloride, mp 320° (with decomposition).

EXAMPLE 2

($R^1$=$CH_3$; $R^2$=$CH_3$; $R^3$=$CH_3$; X=NH)

Analogously to Example 1,1,3,5-trimethyl-4-(2-imidazolin-2-yl)aminopyrazole as the monohydrochloride, mp 260° to 262°, is obtained from 1,3,5-trimethyl-4-aminopyrazole (mp 100° to 101°) via 1,3,5-trimethyl-4-thioureidopyrazole (mp 265° to 267°), its reaction with methyl iodide, followed by reaction with ethylenediamine, cyclization and corresponding processing.

EXAMPLE 3

($R^1$=$CH_3$; $R^2$=$C_2H_5$; $R^3$=$C_2H_5$; X=NH)

Analogously to Example 1, 1-methyl-3,5-diethyl-4-(2-imidazolin-2-yl)aminopyrazole as the monohydrochloride, mp 187° to 188°, is obtained from 1-methyl-3,5-diethyl-4-aminopyrazole hydrochloride (mp 247° to 249°) via 1-methyl-3,5-diethyl-4-thioureidopyrazole (mp 234° to 235°), its reaction with methyl iodide, followed by reaction with ethylenediamine, cyclization and corresponding processing.

EXAMPLE 4

($R^1$=$C_2H_5$; $R^2$=$CH_3$; $R^3$=$CH_3$; X=NH)

Analogously to Example 1, 1-ethyl-3,5-dimethyl-4-(2-imidazolin-2-yl)aminopyrazole as the monohydrochloride, mp 180° to 182°, is obtained from 1-ethyl-3,5-dimethyl-4-aminopyrazole (mp 69° to 70°) via 1-ethyl-3,5-dimethyl-4-thioureidopyrazole (mp 248°), reacting the latter with methyl iodide, followed by reaction with ethylenediamine, cyclization and corresponding treatment.

EXAMPLE 5

($R^1$=p-tolyl; $R^2$=$CH_3$; $R^3$=$CH_3$; X=NH)

Analogously to Example 1, 1p-tolyl-3,5-dimethyl-4-(2-imidazolin-2-yl)aminopyrazole as the monohydrochloride, mp 240°, is obtained from 1p-tolyl-3,5-dimethyl-4-aminopyrazole monohydrate (mp 85° to 87°) via 1-p-tolyl-3,5-dimethyl-4-thioureidopyrazole (mp 240° to 241°), reacting the latter with methyl iodide, followed by reaction with ethylenediamine, cyclization and corresponding processing.

EXAMPLE 6

($R^1$=p-chlorophenyl); $R^2$=$CH_3$; $R^3$=$CH_3$; X=NH)

Analogously to Example 1, 1p-chlorophenyl-3,5-dimethyl-4-(2-imidazolin-2-yl)aminopyrazole as the monohydrochloride, mp 252° to 254° is produced from 1-p-chlorophenyl-3,5-dimethyl-4-aminopyrazole monohydrate (mp 74° to 77°) via 1-p-chlorophenyl-3,5-dimethyl-4-thioureidopyrazole (mp 244° to 246°), reacting the latter with methyl iodide, followed by reaction with ethylenediamine, cyclization and corresponding processing.

EXAMPLE 7

($R^1$=phenyl; $R^2$=$CH_3$; $R^3$=$CH_3$; X=NH)

1-phenyl-3,5-dimethyl-4-thioreidopyrazole (mp 236° to 238°(is obtained from 1-phenyl-3,5-dimethyl-4-aminopyrazole monohydrate (mp 59°) by reaction with ammonium thiocyanate and processing according to the method described in Example 1.

16 g of this thioureido compound and 18.4 g of methyl iodide are dissolved in 100 ml of methanol, and the mixture is heated to boiling under reflux for 2 hours. The resulting solution is concentrated by evaporation; the residue is mixed with 4.8 g of ethylenediamine; and the reaction mixture is cyclized by heating it for 1 hour at 160°. The thus-obtained reaction product is dissolved in approximately 100 ml of water and the produced aqueous solution is washed with diethylether. After adding concentrated (aq) ammonia solution thereto, 1-phenyl-3,5-dimethyl-4-(2-imidazolin-2-yl)aminopyrazole separates out as a finely crystalline precipitate which, after drying, melts at 205° to 207° (with decomposition). The yield is 9.9 g.

EXAMPLE 8

($R^1=CH_3$; $R^2=$phenyl; $R^3=CH_3$; $X=NH$)

Analogously to Example 7, 1,3-dimethyl-5-phenyl-4-(2-imidazolin-2-yl)-aminopyrazole, mp 232° to 234°, (which is converted into the corresponding hydrochloride by reaction with hydrochloric acid) is produced from 1,3-dimethyl-5-phenyl-4-aminopyrazole (mp 138° to 139°C) via 1,3-dimethyl-5-phenyl-4-thioureidopyrazole (mp 258° to 260°), reacting the latter with methyl iodide, followed by reaction with ethylenediamine, cyclization and corresponding processing.

EXAMPLE 9

($R^1=$phenyl; $R^2=$phenyl; $R^3=CH_3$; $X=NH$)

Analogously to Example 7, 1,5-diphenyl-3-methyl-4-(2-imidazolin-2-yl)-aminopyrazole, mp 205° to 208°, is obtained from 1,5-diphenyl-3-methyl-4-aminopyrazole hydrochloride (mp 230° to 233°) via 1,5-diphenyl-3-methyl-4-thioureidopyrazole (mp 212° to 214°), reacting the latter with methyl iodide, followed by reaction with ethylenediamine, cyclization and corresponding processing.

Analogously, from
(a) 1-cyclohexyl-3,5-dimethyl-4-aminopyrazole,
(b) 1-benzyl-3,5-dimethyl-4-aminopyrazole,
(c) 1-o-chlorophenyl-3,5-dimethyl-4-aminopyrazole,
(d) 1-p-fluorophenyl-3,5-dimethyl-4-aminopyrazole,
(e) 1-m-bromophenyl-3,5-dimethyl-4-aminopyrazole,
(f) 1-m-tolyl-3,5-dimethyl-4-aminopyrazole and
(g) 1-p-chlorobenzyl-3,5-dimethyl-4-aminopyrazole
via
(a') 1-cyclohexyl-3,5-dimethyl-4-thioureidopyrazole,
(b') 1-benzyl-3,5-dimethyl-4-thioureidopyrazole,
(c') 1-o-chlorophenyl-3,5-dimethyl-4-thioureidopyrazole,
(d') 1-p-fluorophenyl-3,5-dimethyl-4-thioureidopyrazole,
(e') 1-m-bromophenyl-3,5-dimethyl-4-thioureidopyrazole,
(f') 1-m-tolyl-3,5-dimethyl-4-thioureidopyrazole and
(g') 1-p-chlorobenzyl-3,5-dimethyl-4-thioureidopyrazole, respectively, and reacting each of the latter with methyl iodide, followed by reaction with ethylenediamine, cyclization and corresponding processing,
(a'') 1-cyclohexyl-3,5-dimethyl-4-(2-imidazolin-2-yl)pyrazole,
(b'') 1-benzyl-3,5-dimethyl-4-(2-imidazolin-2-yl)pyrazole,
(c'') 1-o-chlorophenyl-3,5-dimethyl-4-(2-imidazolin-2-yl)pyrazole,
(d'') 1-p-fluorophenyl-3,5-dimethyl-4-(2-imidazolin-2-yl)pyrazole,
(e'') 1-m-bromophenyl-3,5-dimethyl-4-(2-imidazolin-2-yl)pyrazole,
(f'') 1-m-tolyl-3,5-dimethyl-4-(2-imidazolin-2-yl)pyrazole and
(g'') 1-p-chlorobenzyl-3,5-dimethyl-4-(2-imidazolin-2-yl)pyrazole, respectively are produced.

EXAMPLE 10

($R^1=R^2=R^3=CH_3$; $X=O$)

To a solution of 10.0 g of 1,3,5-trimethyl-4-aminopyrazole in 300 ml of tetrahydrofuran under agitation, a mixture of 8.8 g of β-chloroethylisocyanate and 50 ml of tetrahydrofuran is added slowly drop by drop at a temperature between 0° and 5°. The agitation is continued for a further 3 hours without cooling, and then the tetrahydrofuran distilled off in vacuo. The residue is washed with diethylether and dried to obtain 15.5 g (85.7% of theory) of 1,3,5-trimethyl-4-($N^2$-β-chloroethyl)ureidopyrazole, mp 152° to 153°.

11.8 g of thus-obtained ureido compound are suspended in 100 ml of water. After adding thereto a small quantity of a commercial wetting agent, the resulting suspension is poured into 900 ml of boiling water. The prepared mixture is heated to boiling for 15 minutes and then rapidly cooled to produce a solution which is then concentrated to about one-quarter of its volume in vacuo and washed with methylene chloride. The aqueous phase is mixed with an excess of aqueous ammonia solution and exhaustively extracted with methylene chloride. The methylene chloride solution is dried with sodium sulfate and concentrated by evaporation to yield 9.6 g (96.6% of theory) of 1,3,5-trimethyl-4-(2-oxazolin-2-yl)aminopyrazole, mp 131° to 132° (ethyl acetate/diethyl ether).

EXAMPLE 11

($R^1=C_2H_5$; $R^2=R^3=CH_3$; $X=O$)

Analogously to Example 10, 1-ethyl-3,5-dimethyl-4X=2-oxazolin-2-yl)aminopyrazle, mp 99° to 100°, is obtained from 1-ethyl-3,5-dimethyl-4-aminopyrazole (mp 69° to 70°) and β-chloroethylisocyanate [yielding 1-ethyl-3,5-dimethyl-4-($N^2$-β-chloroethyl)ureidopyrazole (mp 140° to 141°)] and cyclizing the latter.

EXAMPLE 12

($R^1=$cyclohexyl; $R^2=R^3=CH_3$; $X=O$)

Analogously to Example 10, 1-cyclohexyl-3,5-dimethyl-4-(2-oxazolin-2-yl)-aminopyrazole, mp 136° to 138°, is obtained from 1-cyclohexyl-3,5-dimethyl-4-aminopyrazole (mp 68° to 69°) and β-chloroethylisocyanate [yielding 1-cyclohexyl-3,5-dimethyl-4-($N^2$-β-chloroethyl)ureidopyrazole (mp 150° to 151°)] and cyclizing the latter.

EXAMPLE 13

($R^1$=CH$_3$; $R^2$=phenyl; $R^3$=CH$_3$; X=O)

Analogously to Example 10, 1,3-dimethyl-5-phenyl-4-(2-oxazolin-2-yl)aminopyrazole, mp 188° to 190°, is produced from 1,3-dimethyl-5-phenyl-4-aminopyrazole (138° to 139°) and β-chloroethylisocyanate [yielding 1,3-dimethyl-5-phenyl-4-($N^2$-β-chloroethyl)-ureidopyrazole (mp 220° to 221°)] and cyclizing the latter.

EXAMPLE 14

($R^1$=CH$_3$; $R^2$=$R^3$=phenyl; X=O)

Anaologously to Example 10, 1-methyl-3,5-diphenyl-4-(2-oxazolin-2-yl)aminopyrazole, mp 206° to 208°, is obtained from 1-methyl-3,5-diphenyl-4-aminopyrazole (mp 80° to 81°) and β-chloroethylisocyanate [yielding 1-methyl-3,5-diphenyl-4-($N^2$-β-chloroethyl-)ureidopyrazole (mp 207° to 208°)] and cyclizing the latter.

EXAMPLE 15

($R^1$=phenyl; $R^2$=$R^3$=CH$_3$; X=O)

Analogously to Example 10, 1-phenyl-3,5-dimethyl-4-(2-oxazolin-2-yl)aminopyrazole, mp 122° to 124°, is obtained from 1-phenyl-3,5-dimethyl-4-aminopyrazole monohydrate (mp 59°) and β-chloroethylisocyanate [yielding 1-phenyl-3,5-dimethyl-4-($N^2$-β-chloroethyl-)ureidopyrazole (mp 140° to 141°)] and cyclizing the latter.

EXAMPLE 16

($R^1$= $R^2$=phenyl; $R^3$=CH$_3$; X=O)

Analogously to Example 10, 1,5-diphenyl-3-methyl-4-(2-oxazolin-2-yl)aminopyrazole, mp 194° to 196°, is obtained from 1,5-diphenyl-3-methyl-4-aminopyrazole (mp of the hydrochloride: 230° to 233°) and β-chloroethylisocyanate [yielding 1,5-diphenyl-3-methyl-4-($N^2$-β-chloroethyl)ureidopyrazole (mp 144° to 146°)] and cyclizing the latter.

EXAMPLE 17

($R^1$=benzyl; $R^2$=$R^3$CH$_3$; X=O)

Analogously to Example 10, 1-benzyl-3,5-dimethyl-4-(2-oxazolin-2-yl)aminopyrazole, mp 129° to 130°, is obtained from 1-benzyl-3,5-dimethyl-4-aminopyrazole (mp of the hydrochloride: 225° to 227°) and β-chloroethylisocyanate [yielding 1-benzyl-3,5-dimethyl-4-($N^2$-β-chloroethyl)ureidopyrazole (mp 151° to 152°)]and cyclizing the latter.

EXAMPLE 18

($R^1$=CH$_3$; $R^2$=CH$_3$; $R^3$=CH$_3$; X=NH)

19.0 g of 1,3,5-trimethyl-4-aminopyrazle are dissolved in 152 ml of 1 N hydrochloric acid. After adding 38 g of finely-powdered calcium carbonate and 100 ml of ethylene chloride to the resulting solution, 20.7 g of thiophosgene are added drop by drop at room temperature within 4 houtrs, accompanied by vigorous agitation. The agitation is contined for a further 1 hour and then the thus-produced precipitate is filtered off. The liquid phases of the filtrate are separated; the ethylene chloride solution is dried and then evaporated to dryness. The residue (after evaporation) is recrystallized from ligroin to yield 19.5 g (77% of theory) of 1,3,5-trimethyl-4-isothiocyanatopyrazole, mp 51°.

A solution of 9.0 g of the obtained isothiocyanate is 20 ml of benzene is added drop by drop at approximately 10° within 5 hours to a well-agitated mixture of 16.2 g of ethylenediamine and 200 ml of benzene. The precipitated reaction product is filtered off and recrystallized from dimethylglycol to yield 7.9 g (65% of theory) of 1-(β-aminoethyl)-3-(1,3,5-trimethylpyrazole-4-yl)thiourea, mp 128°.

A solution of 7.0 g of the thus-prepared thiorea in 100 ml of ethanol is mixed with 10.3 g of mercuric oxide. The resulting suspension is stireed for 8 hours at boiling temperature and then filtered. The filtrate is evaporated to dryness, and the resiude is recrystallized from an ethanol/cyclohexane mixture to yield 3.8 g (64% of theory) of 1,3,5-trimethyl-4-(2-imidazolin-2-yl)aminopyrazole, mp 227° to 230° (decomposition).

EXAMPLE 19

1.00 g of 1-ethyl-3,5-dimethyl-4-(2-oxazolin-2-yl)aminopyrazole is dissolved together with 0.56 g of furmaric acid in a little methanol. The solution is evaporated to dryness, and the evaporation residue is washed several times with diethylether to obtain 1.50 g of 1-ethyl-3,5-dimethyl-4-(2-oxazolin-2-yl)aminopyrazole hydrogen fumarate, mp 107° to 109°.

EXAMPLE 20

1.00 g of 1,3-dimethyl-5-phenyl-4-(2-oxazolin-2-yl)aminopyrazole is dissolved in a little methanol, and ethanolic hydrochloric acid is added thereto until a weakly acid reaction is obtained. The resulting solution is evaporated to dryness, and the evaporation residue is washed several times with diethylether to obtain 1.15 g of 1,3-dimethyl-5-phenyl-4-(2-oxazolin-2-yl)aminopyrazole hydrochloride, mp 211° to 213°.

EXAMPLE 21

10.0 g of 1,3-dimethyl-4-amino-5-phenylpyrazole, 11.2 g of 1-benzoyl-2-imidazolidin-2-one and 78 ml of phosphorus oxychloride are stirred for 20 hours at 50° C. The excess phosphorus oxychloride is distilled off in vacuo. The residue is stirred with ice and water for one hour, alkalized with sodium hydroxide solution and further cooled by means of ice. The separated reaction product is extracted with chloroform, and the chloroform solution is washed to neutrality with water, dried and evaporated. The residue (18.1 g) is recrystallized from isopropyl alcohol to yield 12.4 g (64.6% of theory) of 1,3-dimethyl-5-phenyl-4-(1-benzoyl-2-imisazolin-2-yl)aminopyrazole, mp 207° to 209°.

10.0 g of 1,3-dimethyl-5-phenyl-4-(1-benzoyl-2-imidazolin-2-yl)aminopyrazole are heated to boiling in methanol under reflux for 6 hours. The solvent (methanol) is distilled off in vacuo, and the residue is twice recrystallized from isopropyl alcohol to yield 5.7 g (80.2% of theory) of 1,3-dimethyl-5-phenyl-4-(2-imidazolin-2-yl)aminopyrazole, mp 232° to 234°. The mixed melting point with the product obtained in accordance with Example 8 shows no depression.

EXAMPLE 22

12.5 g of 1,3,5-trimethyl-4-aminopyrazole, 20.9 g of 1-benzoyl-2-imidazolidin-2-one and 140 ml of phosphorus oxychloride are stirred for 20 hours at 50°. The excess phosphorus oxychloride is evaporated in vacuo. The residue is dissolved in 400 ml of methanol and heated to boiling under reflux for 4 hours. The solvent is distilled off, the residue dissolved in 150 ml of isopropyl alcohol, and the solution mixed at 0° with ethanolic hydrochloric acid until precipitation ends. After adding 150 ml of diethylether, the obtained precipitate is filtered and washed with isopropyl alcohol/diethylether to obtain 17.4 g (75.8% of theory) of 1,3,5-trimethyl-4-(2-imidazolin-2-yl)aminopyrazole hydrochloride, mp 260° to 262°. The mixed melting point with the product obtained in accordance with Example 2 shows no depression.

PHARMACEUTICAL FORMULATIONS
EXAMPLE 23

| Batch for 100 liters | |
|---|---|
| 1.) 1,5-diphenyl-3-methyl-4-(2-imiadazolin-2-yl)aminopyrazole | 1.913 kg |
| 2.) Methanesulfonic acid | 0.579 kg |
| 3.) Mannitol | 3.253 kg |
| 4.) Double-distilled water | up to 100 liters |

About 90 liters of 4 are heated to 50°. Then, first 1 and 2 and then 3 are dissolved in this. After cooling, the resulting solution is made up to 100 liters with 4. The solution is filtered under sterile conditions and filled in 5-ml ampoules, which are sterilized for 1 hour at 100°.

EXAMPLE 24

| Batch for 150,000 tablets: | |
|---|---|
| 1.) 1,3,5-trimethyl-4-(2-imidazolin-2-yl)aminopyrazole (as the hydrochloride) | 450 g |
| 2.) Urapidil | 3750 g |
| 3.) Lactose | 13950 g |
| 4.) Maize starch | 7650 g |
| 5.) Kollidon 25 (PVP) | 900 g |
| 6.) Primojel | 2250 g |
| 7.) Talcum | 750 g |
| 8.) Magnesium stearate | 300 g |
| | 30000 g |

Production: 1, 13000 g of 3 and 7000 g of 4 are weighed out. 2 and the rest of 3 are rubbed down. All this is dissolved with 5 and the rest of 4 in about 4.5 liters of ethanol and granulated. The granulate is pre-dried in a drying cabinet and then passed through a sieve [mesh width: 1.25 millimeters (mm)]. After drying (without heating), 6, 7 and 8 are added, and the resulting mixture is mixed in a mixing machine for 15 minutes. The obtained granulate is pressed into 8-mm-diameter tablets, each having a weight of 200 milligrams (mg).

EXAMPLE 25

| Batch for 150,000 tablets: | |
|---|---|
| 1.) 1,3,5-trimethyl-4-(2-imidazolin-2-yl)-aminopyrazole (as the hydrochloride) | 18750 g |
| 2.) Lactose | 7050 g |
| 3.) Maize starch | 4500 g |
| 4.) Kollidon 25 | 900 g |
| 5.) Primojel | 2250 g |
| 6.) Talcum | 750 g |
| 7.) Magnesium stearate | 300 g |
| | 34500 g |

1, 2 and 3 are weighed out. They are then granulated together with 4 (dissolved in 4.5 liters of water). The resulting granulate is pre-dried in a drying cabinet at 50°, passed through a sieve (1.25-mm diameter) and then post-dried at 50° to a moisture content of about 45 to 50%. After adding 5, 6 and 7 thereto, the obtained granulate is mixed for 15 minutes in a mixer and then pressed into 9-mm-diameter tablets, each weighing 230 mg.

EXAMPLE 26

| Batch for 150,000 tablets: | |
|---|---|
| 1.) 1,3,5-trimethyl-4-(2-oxazolin-2-yl)-aminopyrazole (as the hydrochloride) | 18750 g |
| 2.) Lactose | 7050 g |
| 3.) Maize starch | 4500 g |
| 4.) Kollidon 25 | 900 g |
| 5.) Primojel | 2250 g |
| 6.) Talcum | 750 g |
| 7.) Magnesium stearate | 300 g |
| | 34500 g |

1, 2 and 3 are weighed out. They are then granulated together with 4 (dissolved in 4.5 liters of water). The resulting granulate is pre-dried in a drying cabinet at 50°. passed through a sieve (1.25-mm diameter) and then post-dried at 50° to a moisture content of about 45 to 50%. After adding 5, 6 and 7 thereto, the obtained granulate is mixed for 15 minutes in a mixer and then pressed into 9-mm-diameter tablets, ech weighing 230 mg.

PHARMACOLOGY

From the following Table 1 it can be seen that the compounds according to the invention have a distinct antihypertensive action.

The compounds were administered in the stated doses (1 – 5 mg/kg) once daily on two successive days by means of probang to rats with hypertension caused genetically or renally. The measurement of blood pressure and heart rate was effected in each case 2, 6 and 24 hours after administration of the substance. With reference to the maximum blood pressure lowering, the compounds act more strongly antihypertensively than dihydralazine; it is to be noted that the duration of action of the individual compounds is not inferior to that of dihydralazine and in some cases it even far surpasses dihydralazine's duration of action.

Also in regard to the influencing of the heart rate the compounds according to the invention are superior to dihydralazine. Dihydralazine increases the heart rate, the compounds according to the invention lower it. This finding is of great practical significance since dihydralazine's heart rate accelerating action, as sign of a general hyperdynamic circulation phenomenon, restricts the clinical value of this product. (Cf. S. Goodman and A. Gilman: "The pharmacological basis of therapeutics", 5th Edition, Macmillan Publishing Inc., New York, 1975).

The diuretic and electrolyte-excretory action of the compounds according to the invention follows from Table 2. For the investigations male rats were used, the average animal weight of which was about 190 g. Per chemical compound, groups of 12 animals each were formed which were kept in pairs in diureses cages for up to 7 hours after administration of the substance. About 16 hours before commencement of the experiment, food was withheld from the animals; they received water and libitum. During the experiment the animals received neither water nor food.

The compounds were administered as suspension in 0.9% strength NaCl solution by means of probang (orally). The injection volume was 50 ml/kg. An 0.9% strength NaCl solution containing no active compound was administered orally to the control group. The urine was collected intermittently (2, 5 and 7 hours). The 5-hour values are stated.

Sodium and potassium were determined by flame photometry; chloride was titrated coulometrically through silver ions.

The individual measured values were referred to the respective control values (=100). For clearer respresentation, the quotients Na$^+$/K$^+$ of the fractions stated were also referred to the respective controls [($\varrho$compound/$\varrho$control) × 100].

The compounds according to the invention accordingly exhibit a higher diuretic and saluretic activity and/or have a more favourable Na/K quotient (potassium excretion in proportion to sodium excretion more weakly increased) than the comparison compounds.

It should be remarked that the compound 3-methyl-1,5-diphenyl-4-[(2-imidazolin-2-yl)amino]-pyrazole, from a dose of 12.5 mg/kg, inhibits excretion of water and electrolyte.

Table 1

Influence on the systolic blood pressure (mm Hg) and the heart rate (beats/min.) of the awake rat with hypertension caused genetically (= g) or renally (= r) after oral administration in the course of two days    N = number of animals

| Compound | N | mg/kg orally daily | Type of hypertension | Blood pressure mm Hg before administration of substance | mm Hg lowing =max.lowering within 2 days | Heart rate before administration of substance beats/min. | changes at the point in time of max. blood pressure lowering |
|---|---|---|---|---|---|---|---|
| I | 8 | 5.0 | r | 210 | 32 | 381 | −27 |
| II | 8 | 5.0 | g | 199 | 79 | 390 | −110 |
| III | 8 | 2.5 | r | 207 | 57 | 375 | −77 |
|  |  | 1.0 | g | 208 | 40 | 341 | −15 |
| IV | 8 | 5.0 | g | 200 | 36 | 368 | −19 |
| Dihydralazine | 8 | 5.0 | g | 191 | 36 | 370 | +Δ |

I  3,5-Diethyl-1-methyl-4-(2-imidazolin-2-yl)-amino-pyrazole
II  1,3,5-Trimethyl-4-(2-imidazolin-2-yl)-amino-pyrazole
III  1,3,5-Trimethyl-4-(2-oxazolin-2-yl)-amino-pyrazole
IV  3-Methyl-1,5-diphenyl-4-(2-imidazolin-2-yl)-amino-pyrazole

Table 2

| compound | Dose ]mg/kg] | ml urine per kg | meq Na per kg | meq Cl per kg | Na/K | |
|---|---|---|---|---|---|---|
| I | 0.375 | 115 | 121 | 108 | 116 | 111 |
|  | 0.75 | 192 | 182 | 117 | 170 | 155 |
|  | 1.50 | 246 | 231 | 113 | 203 | 204 |
|  | 3.00 | 265 | 236 | 110 | 208 | 214 |
| II | 0.375 | 110 | 122 | 109 | 114 | 111 |
|  | 0.75 | 122 | 136 | 95 | 124 | 143 |
|  | 1.50 | 132 | 133 | 91 | 122 | 145 |
|  | 2.00 | 159 | 169 | 110 | 154 | 152 |
| III | 0.75 | 115 | 117 | 89 | 113 | 131 |
|  | 1.50 | 15f | 161 | 107 | 146 | 150 |
|  | 3.0 | 228 | 226 | 123 | 194 | 184 |
|  | 12.5 | 289 | 290 | 168 | 255 | 173 |
| IV | 0.75 | 118 | 125 | 108 | 121 | 116 |
|  | 1.50 | 151 | 143 | 112 | 135 | 127 |
|  | 6.0 | 203 | 207 | 137 | 187 | 151 |
|  | 12.5 | 238 | 239 | 155 | 209 | 155 |
| Spironolactone | 12.5 | 111 | 102 | 87 | 97 | 118 |
|  | 25.0 | 156 | 149 | 113 | 142 | 131 |
|  | 50.0 | 160 | 145 | 113 | 139 | 128 |
| Hydrochlorothiazide | 3.0 | 162 | 165 | 128 | 170 | 129 |
|  | 6.0 | 164 | 170 | 130 | 165 | 130 |
|  | 25.0 | 174 | 176 | 143 | 168 | 123 |

I : 1,3,5-Trimethyl-4-[(2-oxazolin-2-yl)-amino]-pyrasole
II : 1,3-Dimethyl-5-phenyl-4-[(2-xoazolin-2-yl)-amino]-pyrazole
III : 3,5-Dimethyl-4-[(2-imidazolin-2-yl)-amino]-pyrazole
IV : 1,3,5-Trimethyl-4-[(2-imidazoline-2-yl)-amino]-pyrazole

Example 27

| | |
|---|---|
| 3,5-dimethyl-4-(2-imidazolin-2-yl)aminopyrazole as the hydrochloride | 0.1g |
| Citric acid | 1.5g |
| Aluminum chloride | 0.4g |
| Polyvinylpyrrolidone (PVP) | 0.3g |
| Isopropylmyristate | 4.0g |
| Ethanol (96%) | 85.0g |
| Water and perfume | Up to 100.0g |

Example 28

| | |
|---|---|
| 1,3,5-trimethyl-4-(2-imidazolin-2-yl)aminopyrazole | 0.1g |
| Citric acid | 3.0g |
| Polyvinylpyrrolidone (PVP) | 0.5g |
| Isopropylmyristate | 2.5g |
| Ethanol(96%) | 80.0g |
| Water and perfume | Up to 100.0g |

Example 29

| | |
|---|---|
| 3,5-dimethyl-4-(2-imidazolin-2-yl)aminopyrazole | 0.05g |
| Tartaric acid | 2.00g |
| Boric acid | 2.00g |
| Propyleneglycol | 2.00g |
| Ethanol(96%) | 50.00g |
| Water and perfume | Up to 100.00g |

The inventions and their advantages are readily understood from the preceding description. The various changes may be made in the structure of individual compounds and in the components of compositions without departing from the spirit and scope of the inventions or sacrificing their material advantages. The hereinbefore-described compounds and compositions are merely illustrative of preferred embodiments of the inventions.

What is claimed is:

1. A physiologically-active and pharmaceutically-acceptable 4-(2-imidazolin-2-yl)aminopyrazole of the formula

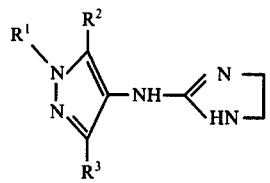

wherein each of $R^1$, $R^2$ and $R^3$ is, independently a hydrogen atom (—H), alkyl having up to 7 carbon atoms, alicyclic hydrocarbyl having from 3 to 7 ring carbon atoms and optionally lower-alkyl substituted, phenyl, substituted phenyl, phenylalkyl or nuclearly-substituted phenylalkyl; the alkyl of phenylalkyl and of substituted phenylalkyl having from 1 to 4 carbon atoms and any substituent of substituted phenyl or of substituted phenylalkyl being a member selected from the group consisting of halo, alkyl having from 1 to 4 carbon atoms, alkoxy having from 1 to 4 carbon atoms, trifluoromethyl and nitro;
or a pharmacologically-acceptable acid-addition salt thereof.

2. A pharmacologically-active and pharmaceutically-acceptable product according to claim 1 wherein: $R^1$ is —H, lower alkyl, cycloalkyl, phenyl, monosubstituted phenyl (the substituent being halo, lower alkyl or lower alkoxy), disubstituted phenyl (the substituents being alike or different and signifying halo, lower alkyl or lower alkoxy), phenylalkyl, monosubstituted phenylalkyl (the substituent being halo, lower alkyl or lower alkoxy), disubstituted phenylalkyl (the substituents being alike or different and signifying halo, lower alkyl or lower alkoxy); and each of $R^2$ and $R^3$ is, independently, lower alkyl, phenyl, monosubstituted phenyl (the substituent being halo, lower alkyl or lower alkoxy), disubstituted phenyl (the substituents being alike or different and signifying halo, lower alkyl or lower alkoxy).

3. A pharmacologically-active and pharmaceutically-acceptable product according to claim 1 wherein: $R^1$ is —H, lower alkyl, cyclohexyl, phenyl, p-chlorophenyl, p-tolyl or benzyl; $R^2$ is lower alkyl or phenyl; and $R^3$ is lower alkyl.

4. A pharmacologically-active and pharmaceutically-acceptable product according to claim 1 wherein: $R^1$ is —H, methyl, ethyl or phenyl; $R^2$ is methyl, ethyl or phenyl; and $R^3$ is methyl or ethyl.

5. A compound according to claim 1 which is 3,5-dimethyl-4-(2-imidazolin-2-yl)aminopyrazole or a pharmacologically-tolerated acid-addition salt thereof.

6. A compound according to claim 1 which is 1,3,5-trimethyl-4-(2-imidazolin-2-yl)aminopyrazole or a pharmacologically-tolerated acid-addition salt thereof.

7. A compound according to claim 1 which is 1-methyl-3,5-diethyl-4-(2-imidazolin-2-yl)aminopyrazole or a pharmacologically-tolerated acid-addition salt thereof.

8. A compound according to claim 1 which is 1,5-diphenyl-3-methyl-4-(2-imidazolin-2-yl)aminopyrazole or a pharmacologically-tolerated acid-addition salt thereof.

9. A pharmaceutical composition having a pilomotoric-effective concentration of at least one active compound according to claim 1 or of a pharmacologically-acceptable acid-addition salt thereof and therapeutically-compatible, non-toxic support or carrier therefor.

10. A pilomotoric composition having an effective concentration of at least one active principle according to claim 1 and suitable cosmetically-acceptable carrier therefor.

11. A process for strengthening hair or making it more erect which comprises applying thereto an effective amount of a product according to claim 1.

* * * * *